United States Patent
Muller

(10) Patent No.: US 10,800,561 B2
(45) Date of Patent: Oct. 13, 2020

(54) PREPARATION OF COFFEE-BASED EXTRACTS AND POWDERS

(71) Applicant: Koffeefruit Pte. Ltd., Singapore (SG)

(72) Inventor: Mark L. Muller, Holualoa, HI (US)

(73) Assignee: Koffeefruit Pte. Ltd., Singapore (SG)

( * ) Notice: Subject to any disclaimer, the term of this patent is extended or adjusted under 35 U.S.C. 154(b) by 912 days.

(21) Appl. No.: 14/846,329

(22) Filed: Sep. 4, 2015

(65) Prior Publication Data

US 2016/0030350 A1 Feb. 4, 2016

Related U.S. Application Data

(63) Continuation of application No. 13/745,159, filed on Jan. 18, 2013, now abandoned.

(60) Provisional application No. 61/589,094, filed on Jan. 20, 2012.

(51) Int. Cl.
| | |
|---|---|
| *B65B 25/00* | (2006.01) |
| *A61K 36/74* | (2006.01) |
| *B65B 31/00* | (2006.01) |
| *A23F 5/00* | (2006.01) |
| *A23L 33/15* | (2016.01) |
| *A23L 33/105* | (2016.01) |
| *A23F 5/26* | (2006.01) |

(52) U.S. Cl.
CPC .............. *B65B 25/001* (2013.01); *A23F 5/00* (2013.01); *A23F 5/26* (2013.01); *A23L 33/105* (2016.08); *A23L 33/15* (2016.08); *A61K 36/74* (2013.01); *B65B 31/00* (2013.01); *A61K 2236/00* (2013.01)

(58) Field of Classification Search
CPC ...... A23F 5/14; A23F 5/02; A23F 5/00; A23L 33/105; A23L 19/07; A23L 19/01; A23L 19/03; A23V 2002/00; A23V 2300/10; A23V 2300/14; A61K 36/74
See application file for complete search history.

(56) References Cited

U.S. PATENT DOCUMENTS

| | | |
|---|---|---|
| 2,557,294 A | 6/1951 | Kellogg et al. |
| 3,725,076 A | 4/1973 | Stefanucci et al. |
| 4,112,130 A | 9/1978 | Gupta |
| 4,316,916 A | 2/1982 | Adamer |
| 5,252,061 A | 10/1993 | Ozer et al. |
| 5,624,699 A | 4/1997 | Lang |
| 6,113,908 A | 9/2000 | Paton et al. |
| 6,159,512 A | 12/2000 | Reyes |
| 6,231,866 B1 | 5/2001 | Mann |
| 6,235,721 B1 | 5/2001 | Ghosal |
| 6,383,550 B1 | 5/2002 | Juillerat et al. |
| 6,528,099 B1 | 3/2003 | Garti et al. |
| 6,861,083 B2 | 3/2005 | Martel et al. |
| 7,000,534 B1 | 2/2006 | Mendes |
| 7,033,623 B2 | 4/2006 | Suzuki et al. |
| 7,175,863 B1 | 2/2007 | Mathias et al. |
| 8,178,148 B2 | 5/2012 | Fujii et al. |
| 8,486,470 B2 | 7/2013 | Laukli et al. |
| 8,784,914 B2 | 7/2014 | Leloup et al. |
| 8,840,948 B2 | 9/2014 | Yamamoto et al. |
| 8,980,362 B2 | 3/2015 | Du et al. |
| 9,084,436 B2 | 7/2015 | Sorensen et al. |
| 9,243,843 B2 | 1/2016 | Savarese |
| 9,422,504 B2 | 8/2016 | Msika et al. |
| 9,879,284 B2 | 1/2018 | Gonzalez Marin et al. |
| 2004/0037938 A1 | 2/2004 | Smith |
| 2006/0263507 A1* | 11/2006 | Miljkovic .................. A23F 3/34 426/596 |
| 2006/0263508 A1 | 11/2006 | Miljkovic et al. |
| 2007/0281048 A1 | 12/2007 | Miljkovic |
| 2009/0104310 A1 | 4/2009 | Nakajima et al. |
| 2009/0175973 A1 | 7/2009 | Vikhrieva |
| 2018/0235251 A1* | 8/2018 | Muller ........................ A23F 5/00 |
| 2018/0289030 A1* | 10/2018 | Muller ........................ A23L 2/52 |

FOREIGN PATENT DOCUMENTS

| | | | | |
|---|---|---|---|---|
| GB | 1203284 A | * | 8/1970 | ............... A23N 5/00 |
| JP | 2000-501947 A | | 2/2000 | |
| JP | 2015-503355 A | | 2/2015 | |
| WO | 87/03951 A1 | | 7/1987 | |
| WO | 02/062159 A1 | | 8/2002 | |
| WO | WO-2015013199 A1 | * | 1/2015 | ............. A23L 19/07 |

OTHER PUBLICATIONS

A.A.Abd El-Moneinn E, et al "Effect of Honey and Citric Acid Treatments on Postharvest Quality of Fruits and Fresh-Cut of Guava" World J. Agric. Sci., 11 (5): 255-267, 2015 (Year: 2015).*
Baldwin EA "Surface Treatments and Edible Coatings in Food Preservation" Handbook of Food Preservation, Second Edition (Rahman MS, Ed.), Chapter 21, pp. 477-507, ISBN—13: 978-1574446067. (Year: 2007).*
Rathinavelu R, et al "Potential alternative use of coffee wastes and by-products" Use of coffee wastes and by-products: A summary, Aug. 17, 2005,E1967/05,pp. 1-4. (Year: 2005).*
Baldwin EA et al :Improving storage life of cut apple and potato with edible coating Postharvest Biology and Technology,1996,9, pp. 15I-163. (Year: 1996).*
Rojas-Grau MA, et al "Edible coatings to incorporate active ingredients to freshcut fruits: a review" Trends in Food Science & Technology,2009,20,pp. 438-447. (Year: 2009).*
Santerre CR, et al "Ascorbic Acid/Citric Acid Combinations in the Processing of Frozen Apple Slices" J. Food Sci.,1988,53(6), pp. 1713-1716. (Year: 1988).*

(Continued)

*Primary Examiner* — Aaron J Kosar
(74) *Attorney, Agent, or Firm* — Howard & Howard Attorneys PLLC

(57) ABSTRACT

Processes for preparing antioxidant-rich compositions, for example from coffee cherries, are disclosed. These processes can involve promptly contacting de-beaned coffee cherries with a preservative coating, and optionally storing under refrigerated conditions, prior to the preparation of an extract or powder.

33 Claims, 3 Drawing Sheets

(56) References Cited

OTHER PUBLICATIONS

Clifford et al. (1991) "Phenols and caffeine in wet-processed coffee beans and coffee pulp", Food Chemistry, 40(1): 35-42.
Clifford (1986) "Coffee bean dicaffeoylquinic acids", Phytochemistry, 25(7): 1767-1769.
Baiq Rien Handayani (2009) "Study and characterization of antibacterial compounds of Arabica coffee berry pulp" PhD Thesis , 98 pp.
Stalmach et al. (2009) "Metabolite Profiling of Hydroxycinnamate Derivatives in Plasma and Urine 20, after the Ingestion of Coffee by Humans: Identification of Biomarkers of Coffee Consumption", Drug Metabolism and Disposition, 37(8): 1749-1758.
Fresco et al. (2006) "New Insights on the Anticancer Properties of Dietary Polyphenols", Medicinal 42 Research Reviews, 26(6): 747-766.
Molina, et al., (1974) Turrialba, 24(3): 280-284.

\* cited by examiner

PREPARATION OF COFFEE-BASED EXTRACTS AND POWDERS

CROSS-REFERENCE TO RELATED APPLICATIONS

This application is a continuation of U.S. application Ser. No. 13/745,159, filed Jan. 18, 2013, which application claims the benefit of priority to U.S. Provisional Application No. 61/589,094, filed Jan. 20, 2012, teachings of which are hereby incorporated by reference.

TECHNICAL FIELD

The invention relates generally to processes for isolating and extracting antioxidants and other beneficial compounds from coffee cherries.

BACKGROUND

The fruit of the coffee plant (e.g., *Coffea arabica*) is often called the "coffee cherry." The coffee cherry is made up of the following layers (from the outside in): skin, pulp, mucilage, parchment and bean. The skin, also referred to as the epicarp or exocarp, is a monocellular layer covered with a waxy substance ensuring protection of the fruit. The mesocarp includes the pulp and the mucilage. The pulp is the fleshy outer layer of the mesocarp, directly beneath the skin, which during processing can be removed with a pulping machine. The mucilage is the slimy layer found between the pulp and parchment, adhering to the parchment inside a coffee cherry. It is generally not removed by pulping. Mucilage is not present in unripe coffee fruit, and disappears in overripe coffee. The endocarp, or "parchment," is the tough integument tightly pressed to the bean when fresh but from which the bean shrinks during drying. It lies between the fleshy part (or pulp) of the cherry and the silver skin. The endocarp also includes the thin, crumbly paper-like covering that is left on wet-processed coffee beans after pulping and fermentation, and which is subsequently removed during hulling. The bean includes the endosperm and the embryo. The endosperm includes the tissues that feed the embryo during germination. The embryo ultimately forms the coffee beans. The silver skin is the seminal integument covering the endosperm, i.e., the thin, papery, shiny layer immediately surrounding the coffee bean, being the remnant of the integument. During processing, milling before export removes most silver skin, and the remainder is removed during roasting in the form of chaff. The endosperm fills the integument as the coffee cherry ripens.

The coffee cherry is harvested and processed to make coffee. During processing, the bean portion of the cherry is removed and further processed using various techniques. This processing generally removes the bean, silver skin and parchment. Thus, after the bean is removed, a significant amount of the coffee cherry fruit remains.

Traditionally, the portion of the cherry remaining after the bean is removed is viewed as waste, although it is sometimes processed into compost or animal feed. However, this remaining portion has significant nutritive value. In particular, it is high in antioxidants and polyphenols, including chlorogenic acids of various types, caffeic acid, quinic acid, ferulic acid, proanthocyanidins and others. These compounds have antioxidant activity, which can contribute to good heath by reducing oxidative injury and thus ameliorating associated disease states such as diabetes, Alzheimer's disease and certain types of cardiovascular and neurological conditions. The beneficial antioxidative and other properties of such compounds, as well as other beneficial components of the extracts, can also be used to treat other conditions such as skin disorders and the like. Isolating these antioxidants and other beneficial compounds from the de-beaned coffee cherry can be difficult, however. For example, coffee pulp contains high levels of tannins, which bind the protein and make it difficult to extract and precipitate. An additional problem is that the free phenols in coffee pulp become oxidized to quinones. Quinones are oxidizing agents that may oxidize amino acids in coffee cherry proteins. Also, ripe coffee fruit is used during husking, and exposure to oxygen, and also the activity of enzymes, sugars and other components of the coffee cherries, can cause rapid degradation and/or oxidation of these compounds and rapid bacterial growth either prior to or during processing. These degradative processes can begin almost immediately following removal of the bean. As a result, available methods of isolating the beneficial components from coffee cherries have frequently resulted in poor yields and the presence of undesirable side-products.

There remains a need in the art for improved methods of isolating antioxidants and other beneficial compounds from coffee cherries.

DETAILED DESCRIPTION

Figure 1:
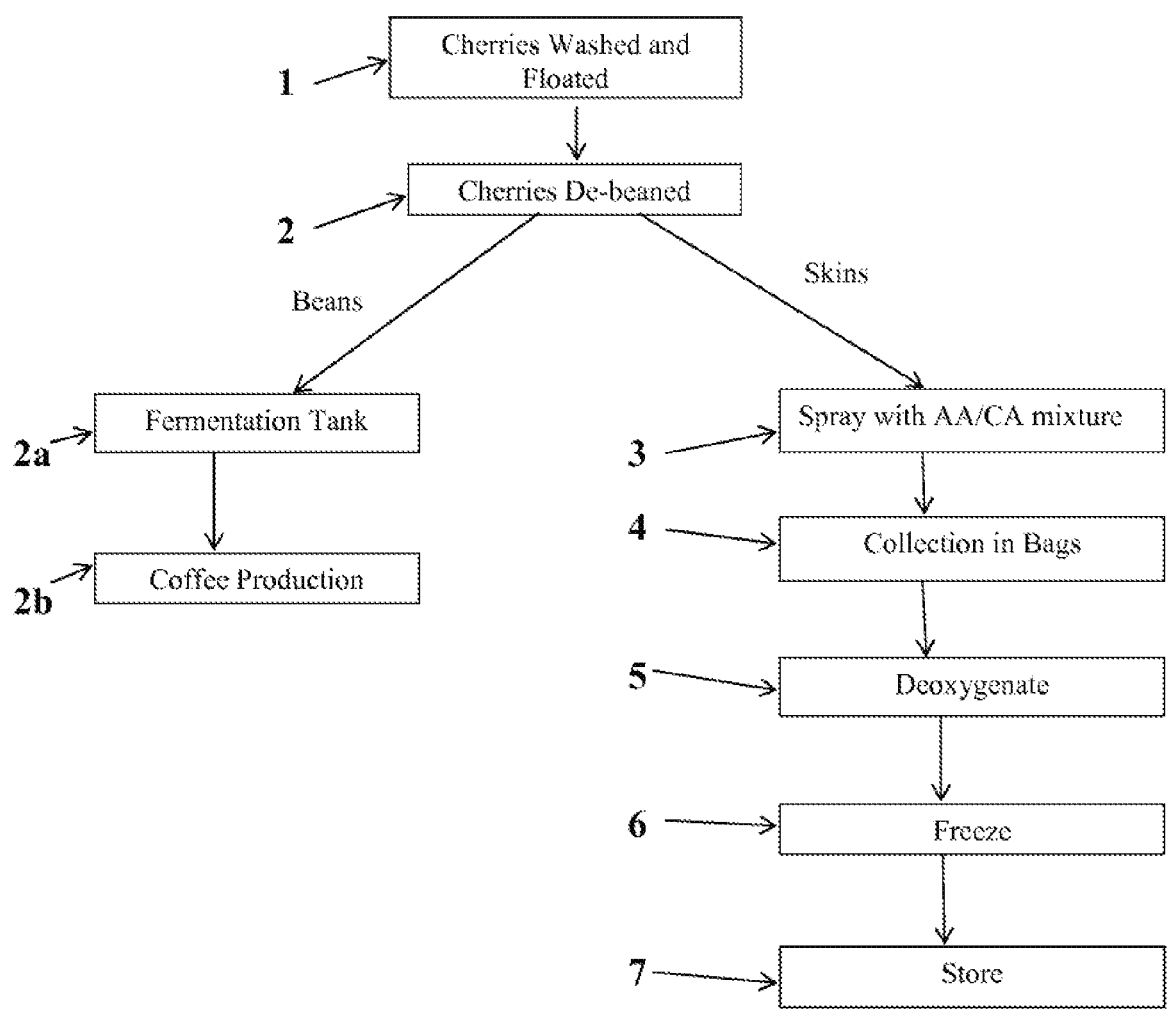
FIG. 1 is a flow chart depicting a de-beaning process that can be used in accordance with the processes disclosed herein. After coffee cherries are received, they are washed and floated in water (1) to eliminate "floaters" (bad cherries float). Cherries are then "de-beaned" (pulped) (2) using a coffee pulping machine which separates the green coffee bean and coffee skin. Green coffee beans are removed to a fermentation/washing tank (2a) and used in coffee production (2c). De-beaned coffee cherries, which can also be referred to herein as coffee pulp or skins, are sprayed with a mixture of ascorbic acid and citric acid (3) via an electric or hand operated sprayer attached to the pulping machine. Coffee skins travel, generally through an auger for a short period of time (<10 seconds) to the coffee skin collection point. There, coffee skins are collected in a poly bag (food grade, airtight) (4). When the receiving container is full the oxygen is removed from the bag (5) using a vacuum, though alternatively a nitrogen or other inert gas flush can be used to remove the oxygen. The bags are immediately closed and sealed to retain the low (or negative) oxygen environment in the container. The sealed, oxygen free/reduced bags of skins are immediately (generally within minutes of pulping) placed into a refrigerated/frozen transport vehicle for immediate refrigeration (6) and transport to freezing facility (7). The bags of oxygen free skins are frozen, generally to a temperature of no greater than 20 to 25 degrees F. to denature the degrading enzymatic activity.
Figure 2:
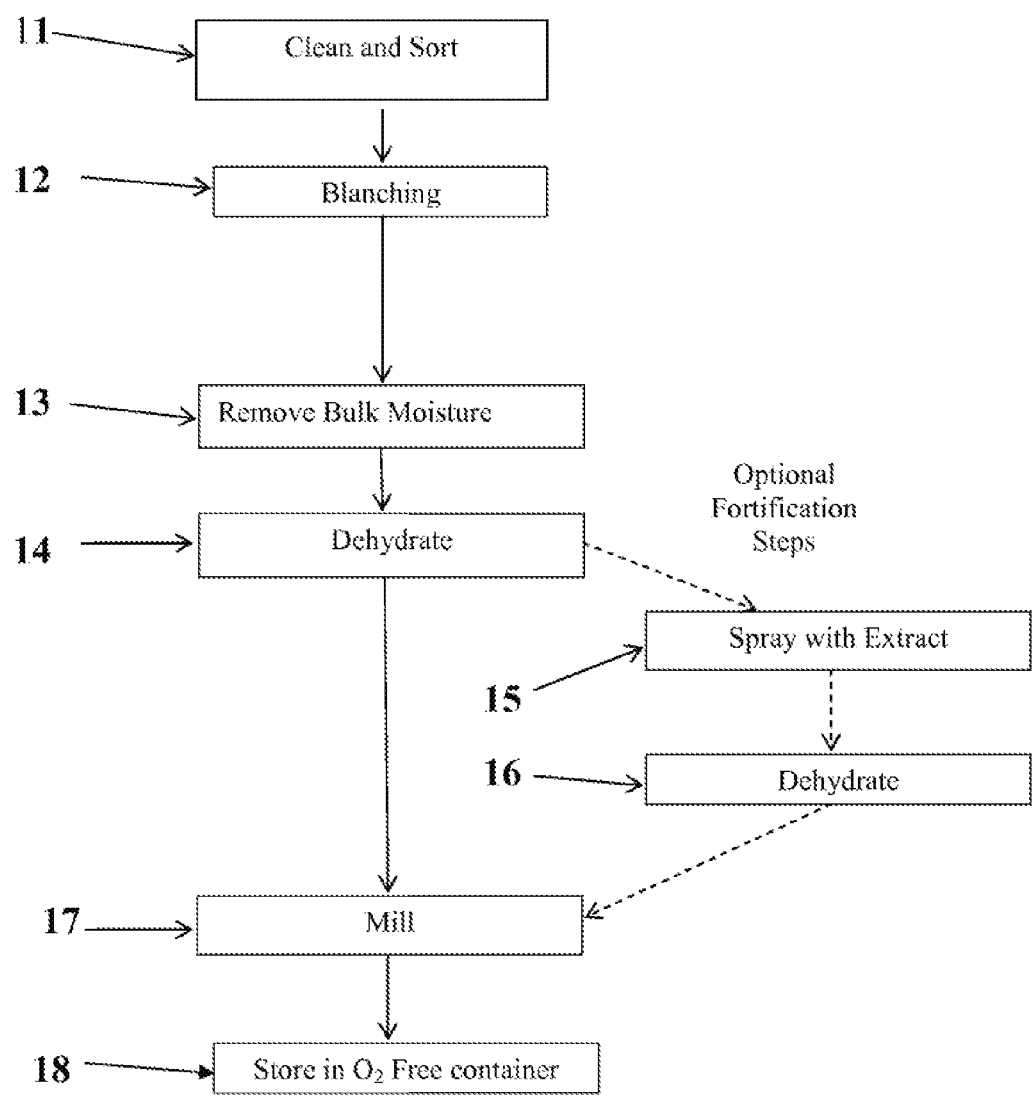
FIG. 2 is a flow chart depicting a representative process for preparing a powder from de-beaned coffee cherries. In this process, de-beaned coffee cherries are received either fresh (i.e., as early as after step 2 of the de-beaning process set forth in FIG. 1, and as late as after step 5) or frozen (i.e., after all steps of FIG. 1). While fresh or still under refrigeration (approximately 20-32 degrees F.) the coffee skins are spread onto perforated drying racks (food grade) and are cleaned of any debris, discolored fruits, leaves, or stems (11). The rack containing the cleaned, treated skins is submersed into a container of water containing a mixture of citric acid/ascorbic acid, or alternatively could be treated using the process of "steam blanching", or by microwave blanching (12). Blanching is the exposure of the coffee skins to boiling water or steam for a brief period of time to inactivate enzymes. Generally, vegetables (except herbs and green peppers) need to be blanched and promptly cooled prior to freezing, since heating slows or stops the enzyme action, which causes vegetables to grow and mature. After maturation, however, enzymes can cause loss in quality, flavor, color, texture, and nutrients. If vegetables are not heated sufficiently, the enzymes will continue to be active during frozen storage and may cause the vegetables to toughen or develop off-flavors and colors. Blanching also causes wilting or softening of vegetables, making them easier to pack. It destroys some bacteria and helps remove any surface dirt. Blanching in hot water at 70 to 105° C. can cause the destruction of enzyme activity. Blanching is usually carried out between 75 and 95° C. for <1 minute. These blanching/treating steps can help to ensure there is no enzymatic activity during the dehydration process. The rack of treated coffee fruit is conveyed through an oxygen free conveyor that has a section in the conveyor that acts as a vibrator/shaker to remove excess moisture from the coffee fruit before dehydration (13). The rack of coffee fruit is loaded into a dehydrator that can operate at low temperature and no or low oxygen. For example, oxygen can be replaced with inert gas. Skins are dehydrated at a temperature that preferably does not exceed 140 degrees F. and continues until a moisture level of approximately 5-6% is achieved (14). At this point the dried coffee fruit can be either stored as whole dried coffee fruit skins, or enriched with a measured spray containing coffee fruit liquid extract (15) and then re-dehydrated to approximately 5-6% moisture (16). After dehydration the coffee fruit skins are either stored or further processed to a powdered form based on market desires using a powder creating machine such as a Fitzmill (17). The process of powdering the skins is carried out in an enclosed environment with oxygen being replaced with Nitrogen or other inert gas. Processed coffee skins are stored in sealed food grade containers that have substantially all the oxygen in the container removed, for example flushed out with nitrogen, and stored in a cool dark environment (18). The containers can then be transported to the factory for processing or to the freezer, which may or may not be located at the processing facility.
Figure 3:
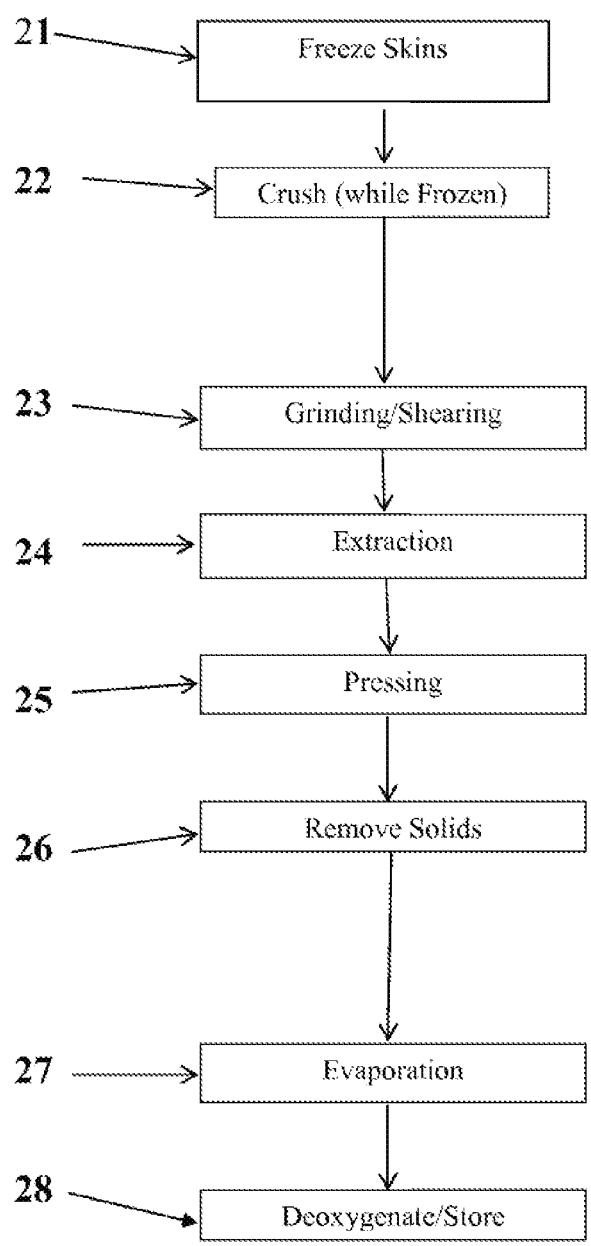
FIG. 3 is a flow chart depicting a representative process for preparing a liquid extract from de-beaned coffee cherries. Treated coffee skins are received frozen in an airtight vacuum (21) after storage as depicted in FIG. 1. Fresh skins are not used because freezing (other than quick freezing) promotes lysis in the cherry skin cell walls which enhances extractions. While still under a refrigerated environment (below 32 degrees F.) each frozen bag of skins is crushed (22) using a press to separate the frozen skins from each other. The bag is removed and the frozen skins are placed on a conveyor to eliminate debris, leaves, and sticks. The skins are conveyed to a receiving tank where the skins are submerged in water that has an initial temperature of up to about 145 degrees F. The receiving tank contains one or more "grinding/shear pumps" (23) that cut the skins to a size consistent for extraction, then pumps the material to an extraction vessel for extraction (24). The extraction vessel contains purified water (alternatively a 50-50 mix of water and methanol/ethanol) that is heated to a temperature up to about 145 degrees and is under a vacuum. The skins can be agitated either mechanically or by other means like ultrasonic vibration. The water-skins ratio is approximately 1:1 (pounds skins:gallons water). Alternatively or additionally, ultra-high pressure extraction (known as UPE) can also be used for extracting phenols and other compounds. The skins, having been extracted, are moved to a "fruit press" (25) which removes the remaining liquid from the coffee skin pulp. The depleted skins are removed. The liquid from the extraction is filtered (26) using either sedimentation, or alternatively using centrifuge apparatus, or membrane filter technology. The filtered liquid extract is reduced to a concentration point where it is stable (approximately 50 BRIX) using an evaporation system (27) with low temperature, no/low oxygen, and low residence time at the evaporator (in exemplary embodiments the product is heated for only approximately 1 second during dehydration, thus preserving nutrients). The resulting liquid extract is packaged and stored in food grade containers, containers to be flushed with nitrogen to remove oxygen and then stored in cool dark conditions (28).

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference as if each had been individually incorporated.

Human cells create "life energy" through oxidation processes; however, excessive oxidation can also cause cell damage. The human body has various systems of controlling oxidation in our cells by using antioxidants. However, because of factors resulting from our highly industrialized society—including pollution, radiation, stress, and our busy lifestyles—our bodies cannot eliminate oxidation as fast as it accumulates causing a vast range of health issues. Reducing oxidation and the oxidation damage from the human body is one of the most important issues for human health. Creating a supply of antioxidant large enough to supply humans on a global scale has been the greatest issue as antioxidant rich materials are difficult to source and expensive to process.

Coffee is the world's second largest agricultural crop, but only a small of its fruit, the bean, is used. Using the present invention, the "by-product" of coffee production, which has previously been viewed as waste, can provide a valuable source of the powerful antioxidants and other beneficial compounds contained in the fruit to make them more readily and abundantly available to the general public.

Process for Preparing Powder

The processes disclosed herein can be used to produce an antioxidant-rich powder, for example from coffee cherries.

The coffee cherries can be at any stage of ripeness that is consistent with the extraction of antioxidants and other beneficial compounds from the coffee cherries. Such antioxidants and other beneficial compounds include, for example, chlorogenic acids of various types, including caffeoylquinic acids (CQA), with 3 isomers (3-, 4- and 5-CQA); dicaffeoylquinic acids (diCQA), with 3 isomers (3,4-diCQA; 3.5-diCQA; 4,5-diCQA); feruloylquinic acids (FQA), with 3 isomers (3-, 4- and S-FQA); p-coumaroylquinic acids (pCoQA), with 3 isomers (3-, 4- and 5-pCoQA), and six mixed diesters of caffeoyl-feruloylquinic acids (CFAQ), with trace amounts of diferuloylquinic acids, dimethoxycinamoylquinic acids, caffeoyl-dimethoxycinamoylquinic acids and feruloyl-dimethoxycinamoylquinic acids; and also prodelphinidins, procyanidins, trigonelline, lignins, tannins such as condensed tannins, hydroxycinnamic acids of various types, coffee saccharides, caffeic acid, quinic acid, ferulic acid, anthocyanins and proanthocyanidins. Chlorogenic acids (CGAs) are a family of esters formed between certain hydroxycinnamic acids and quinic acid. Any such ester is included among the antioxidants and other beneficial compounds noted above. The stage of ripeness is generally reflected by the amount of green coloring that remains on the surface of the coffee cherries, with more green coloring indicating increasingly less ripe. The coffee cherries for use in the processes disclosed herein can be green over, for example, about 50%, about 40%, about 30%, about 20%, about 10%, about 5%, or about 1% of their surface, or the coffee cherries can be ripe, that is, red in color. In exemplary embodiments, the coffee cherries are ripe or nearly ripe (e.g., less than about 10% or less than 5% green on their surface).

The coffee cherries can, for example, be de-beaned prior to further processing, or the entire coffee cherry can be employed. In exemplary embodiments, the coffee cherries are de-beaned. However, wherever "de-beaned coffee cherries" is used herein, a person of ordinary skill in the art would understand that entire coffee cherries can be substituted. Thus, the present invention is particularly applicable to the use of ripe cherries used in a coffee production process after the de-beaning. These cherries are generally viewed as waste from the production process owing to their rapid degradation. As used herein, unless the context indicates otherwise, "skins," when used in reference to coffee fruit, can be understood as equivalent to "de-beaned coffee cherries."

De-beaning the coffee cherries can be done using any method known in the art, such as the methods described herein. Promptly after de-beaning, the surface of the de-beaned coffee cherries is sprayed with a coating such as a preservative coating. For example, as the coffee cherries are de-beaned the de-beaned coffee cherries can be dropped into an auger that transports the coffee cherry to the bagging area. A sprayer can then be used to spray the de-beaned coffee cherries at one end of the auger and the de-beaned coffee cherries can be collected at the other end. The de-beaned coffee cherries can be sprayed before they drop to the auger and are transported on the auger for a brief period, for example approximately 1 (one) minute (though other times can be suitable as disclosed herein) before further processing. The coating can have the effect of inhibiting the degradation of the antioxidants and other beneficial compounds in the coffee, for example by preventing oxidation or enzymatic degradation. For example, phenolic compounds in the fruit can be oxidized by an enzyme called polyphenol oxidase (PPO). This process is evidenced by the browning of the fruit. Also, coffee fruit enzymes are active they can convert free phenols and amino acids to quinic acid. The coating retards these degradative processes, thus preserving higher amounts of antioxidants.

The coating can include, for example, one or more of ascorbic acid, citric acid, acetic acid, benzoic acid, sulfur dioxide, sulfites such as potassium sulfite or combinations of two or more of these compounds. For example, the coating includes a combination of ascorbic acid and citric acid in water or another suitable solvent. For example, the ascorbic acid can be used in an amount of up to or about 1 gram per gallon, 2 grams per gallon, 3 grams per gallon, 4 grams per gallon, 5 grams per gallon, 6 grams per gallon, 7 grams per gallon, 8 grams per gallon, 9 grams per gallon, 10 grams per gallon, 11 grams per gallon, 12 grams per gallon, 13 grams per gallon, 14 grams per gallon, 15 grams per gallon, 20 grams per gallon of water or suitable solvent or more, or about 10-30, about 10-20, or about 12-16 grams per gallon. In some embodiments, powder such as a food-grade powder of ascorbic acid can be used. For example, the ascorbic acid can be present in about 15 grams food grade powder per gallon of water or other suitable solvent.

The citric acid can be used in an amount of up to or about 0.5 grams per gallon, 1 gram per gallon, 2 grams per gallon, 3 grams per gallon, 4 grams per gallon, 5 grams per gallon, 6 grams per gallon, 7 grams per gallon, 8 grams per gallon, 9 grams per gallon, 0.10 grams per gallon, 11 grams per gallon, 12 grams per gallon, 13 grams per gallon, 14 grams per gallon, 15 grams per gallon, 20 grams per gallon or more, or about 1-15, 2-10, or 5-10 grams per gallon. In some embodiments, powder such as a food-grade powder of citric acid can be used.

The ratio of ascorbic acid to citric acid can be from about 4:1 to about 1:4. In exemplary embodiments, ratio of ascorbic acid to citric acid can be about 4:1 to about 1:2, about 3:1 to about 1:1 or about 2:1. For example, the coating can be made up of about 15 grams of ascorbic acid and 7 grams of citric acid per gallon of water. One gallon of the coating can be used to treat about 100-200, about 125-175, or about 150 pounds of de-beaned cherries.

The coating is applied to the de-beaned coffee cherries promptly after harvesting and (in the case of de-beaned coffee cherries) de-beaning. Treating the pulp promptly can serve to denature the enzymes that promote oxidation, thus preserving amino acids and free phenols. As used herein, "promptly" means within a period of time that is consistent with preservation of all or a substantial portion of the antioxidants and other beneficial compounds in the coffee cherry. "Promptly" can mean, for example, within about 24 hours, within about 12 hours, within about 6 hours, within about 4 hours, within about 3 hours, within about 2 hours, within about 1 hour, within about 45 minutes, within about 30 minutes, within about 15 minutes, within about 5 minutes, within about 1 minute, within about 30 seconds, within about 15 seconds, within about 10 seconds, or within about 5 seconds or less after the previous step in the process, or after the event referenced, as applicable. For example, the coating can be applied within about 5 minutes, or within about 1 minute, or within about 30 seconds after harvesting and/or de-beaning. As used herein, "about" means within ten percent (10%) above or below the recited number, unless the context implies otherwise. The coating can be applied, for example, before or as the de-beaned coffee cherries travel through a skin disposal auger.

Depending on the circumstances under which the process is being performed, it may be desirable to store the de-beaned coffee cherries after they are coated but before they are further processed. In such circumstances, the storage can be done under substantially oxygen-free and/or refrigerated conditions. As used herein, "substantially oxygen-free conditions" and "oxygen-free conditions" are used interchangeably and mean conditions under which the de-beaned coffee cherries or processed components thereof are protected against exposure to oxygen in such quantities or activities as to favor the oxidative and/or enzymatic degradation of the antioxidants and/or other beneficial compounds in the de-beaned coffee cherries. Any level of oxygen that fails to produce substantial oxidative and/or enzymatic degradation of antioxidants and/or beneficial compounds is encompassed within "oxygen-free conditions." Oxygen-free conditions can be achieved, for example, by removing most or all oxygen from the environment around the coffee cherries, for example by evacuating and sealing a container holding the coffee cherries, or by replacing oxygen with a different gas, including an inert gas such as nitrogen, argon, carbon dioxide, or combinations thereof. Other means of achieving oxygen-free conditions can also be utilized, for example by immersing the coffee cherries in a fluid with little or no oxygen or oxidative activity, such as a citric acid/ascorbic acid mixture disclosed herein, or lemon juice, sodium metabisulfate solution or sulfur dioxide, or by rendering ineffective or inactive the oxygen that is present in the environment. For example, oxygen-free conditions can be achieved by placing the coffee cherries in one or more containers and evacuating the containers. The containers can be any suitable airtight unit designed for storage, including food-grade poly bags, containment drums with or without liners, trash cans with or without liners, and/or trash/lawn/freezer bags, and can be of any capacity, for example of about 50 lb. capacity. Any step in the processes disclosed herein can be suitable for performing under oxygen-free conditions.

If the de-beaned coffee cherries are to be stored under oxygen-free conditions, the coffee cherries are subjected to such conditions promptly after the cherries are de-beaned, for example within about one minute after de-beaning. For example, the sprayed de-beaned coffee cherries can be sprayed before they drop to the auger, and can then be transported on the auger for approximately 1 (one) minute before being (for example) bagged, vacuumed and sealed.

Whether or not stored under oxygen-free conditions, the coated de-beaned coffee cherries can also be stored under refrigerated conditions. As used herein, "refrigerated conditions" means any conditions of temperature that are effective to inhibit oxidative and/or enzymatic degradation of the antioxidants and other beneficial compounds in coffee cherries. Thus, refrigeration represents one readily and economically achievable method of reducing or eliminating the activity and detrimental effect of any oxygen or residual oxygen in the environment. Refrigerated conditions may also serve to promote cell lysis in the coffee cherries, which promote release of beneficial compounds from the cells, facilitating further processing. Such conditions may also serve to denature enzymes that contribute to degradation of the coffee cherries. For example, "refrigerated conditions" encompasses temperatures lower than about 60° F., about 50° F., about 40° F., about 35° F., about 32° F., about 30° F., about 25° F., about 20° F., about 15° F., about 10° F., about 5° F., about 0° F. or lower. Temperatures below about 32° F. can also be considered freezing conditions. As such, "freezing conditions" is encompassed within "refrigerated conditions." For example, the coated de-beaned coffee cherries can be stored under freezing conditions. If the coated de-beaned coffee cherries are to be stored under refrigerated conditions, they are subjected to such conditions promptly after the cherries are de-beaned, for example within about fifteen minutes, about five minutes, or about two minutes after de-beaning. In exemplary embodiments, preservative coating is applied to the coffee cherries immediately after de-beaning, followed by removal of oxygen and refrigeration. For example, after the coffee cherries are placed in a container, the containers can be placed into a refrigerated transport vehicle such as an ice truck, which exposes the containers to conditions of about 32 degrees F. Storage time in the storage transport vehicle, including during transport to a storage facility, can range from about 5 minutes to several days, for example from about 20 minutes to about three hours. The containers can be transported to a storage facility, which can expose the containers to conditions of about 0-20 degrees F.

Coated de-beaned coffee cherries that are subjected to storage under oxygen-free and/or refrigerated conditions can be stored under such conditions for any length of time that is consistent with preservation of at least a substantial portion of the antioxidants and/or other beneficial compounds in the coffee cherries. Such storage can last, for example, up to about 2 hours, about 4 hours, about 6 hours, about 12 hours, about 24 hours, about 3 days, about one week, about 2 weeks, about one month, about 2 months, about 3 months, about 4 months, about 5 months, about 6 months, about 12 months, about 18 months, about 24 months or longer. For example, such storage can last up to about 6 months, though frozen de-beaned coffee cherries that have reached the time limit can be processed and preserved as dried skins. Should transport be desirable in order to deliver the coffee cherries to a storage facility, such transport can also take place under oxygen-free and/or refrigerated conditions.

De-beaned coffee cherries that were subjected to storage under refrigerated conditions can be crushed, for example by using a hydraulic, mechanical, water, or pneumatic press. This step can serve to evenly spread the de-beaned coffee cherries for inspection and cleaning. Whether or not the coated de-beaned coffee cherries are subjected to storage, the coated de-beaned coffee cherries can then be subjected to an optional further treatment step. This step can be done after the coffee cherries are removed from storage, and can serve to partially or totally thaw the de-beaned coffee cherries that had been stored under refrigerated conditions. The optional further treatment step can be done, for example, under oxygen-free conditions, for example by conducting such operations under a blanket of inert gas. This further treatment step can involve, for example, blanching the coated de-beaned coffee cherries. Blanching can be carried out by exposing the de-beaned coffee cherries to hot water or steam for a period of time. The blanching step can be carried out under any conditions of time and temperature that are consistent with preservation of a substantial portion of the antioxidants and/or other beneficial compounds in coffee cherries. For example, the blanching step can involve exposure to water and/or steam for at least about 15 seconds, 30 seconds, 45 seconds, 1 minute, 2 minutes, 2 minutes 30 seconds, 3 minutes, 3 minutes 30 seconds, 4 minutes, 5 minutes, 10 minutes, 12 minutes, 14 minutes, 15 minutes, 16 minutes, 18 minutes, 20 minutes, 25 minutes, 30 minutes, 1 hour or longer. The hot water and/or steam can be at a temperature of, for example, at least about 120° F., 130° F., 140° F., 150° F., 160° F., 170° F., 180° F., 190° F., 200° F., 210° F., 212° F., 215° F., 220° F., 230° F., 240° F., 250° F., 300° F. or hotter. For example, blanching can be done using either steam or hot water dip using a temperature of approximately 190 F. for a time of approximately 45 seconds to one minute per tray. Though dipping is used here, spraying methods can also be used as a substitute here and also wherever dipping is described herein. In exemplary embodiments, if blanching is conducted in water, the water can contain further preservatives, for example ascorbic acid, citric acid, acetic acid, benzoic acid, sulfur dioxide, sulfites such as potassium sulfite or combinations thereof. After blanching the tray of de-beaned coffee cherries can then be dipped into a second tank consisting of cooler water, which may also containing ascorbic acid, citric acid, acetic acid, benzoic acid, sulfur dioxide, sulfites such as potassium sulfite or combinations thereof, which can provide an immediate cool down of the de-beaned coffee cherries so they don't keep cooking after blanching. The cooler water or solution can also be sprayed onto the de-beaned coffee cherries. Blanching can be done on de-beaned coffee cherries that were frozen and are to be dehydrated. Alternatively or additionally, a blanching step can be done on de-beaned coffee cherries prior to storage, for example after harvest and de-beaning but prior to spraying, or after spraying but prior to refrigeration, or after refrigeration but prior to freezing.

The further treatment step can also involve exposing the coated de-beaned coffee cherries to additional compositions suited to inhibit oxidative and/or enzymatic degradation. Such a composition can include, for example, ascorbic acid, citric acid, acetic acid, benzoic acid, sulfur dioxide, sulfites such as potassium sulfite or combinations thereof. For example, the composition can include ascorbic acid and citric acid in the ratios and in the solvents disclosed herein. For example, the coffee cherries can be exposed to such a composition for at least about 15 seconds, 30 seconds, 45 seconds, 1 minute, 2 minutes, 2 minutes 30 seconds, 3 minutes, 3 minutes 30 seconds, 4 minutes, 5 minutes, 10 minutes, 12 minutes, 14 minutes, 15 minutes, 16 minutes, 18 minutes, 20 minutes, 25 minutes, 30 minutes, 1 hour or longer.

Alternatively, the de-beaned coffee cherries can be transported under refrigerated conditions directly to a production facility, and never delivered to a storage facility for freezing. At the production plant, the de-beaned coffee cherries can then be removed from the scaled bags and spread onto dehydration trays for inspection. They can then be then blanched or solution dipped as described herein, then cold dipped to arrest cooking, then the excess water is shaken off before loading the tray into the dehydrator.

After the optional further treatment step, if any, the coated de-beaned coffee cherries can then be dehydrated. The coffee cherries can be dehydrated to a lower water content, for example to less than about 50%, 40%, 30%, 20%, 10%, 9%, 8%, 7%, 6%, 5%, 4%, 3% or lower, by weight, in water content. For example, the coffee cherries can have a water content of about 5% to about 6% (w/w) after dehydration. Any method known in the art for dehydrating food samples, including any suitable conditions of time and temperature, can be used with the processes disclosed herein. For example, the dehydration can be done under low heat, for example up to or about 100, 110, 120, 125, 130, 135, 140, 145, 150, 160, 180 or 200 degrees F. or higher, or about 100-200, about 120-170, about 130-160, about 130-150 degrees F. The dehydration can be done for a period of time, for example at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 24 hours, 48 hours or longer. For example, dehydration can be done at a temperature of about 130 to about 145 degrees F., or about 135 degrees F., for about 10-12 hours, or until a water content of about 5% or 6% is achieved. In exemplary embodiments, the dehydration step can be carried out under oxygen-free conditions, for example by exposing the coffee cherries to an inert gas such as nitrogen during dehydration. The de-beaned coffee cherries can be conveyed to the dehydrator using a shaker/vibrator conveyor, or loaded directly into the dehydrator.

After dehydration, the coffee cherries can be subjected to an optional enrichment step. This enrichment step can involve contacting the dehydrated coffee cherries with an enriching substance, such as a coffee cherry extract prepared using the processes disclosed herein and described further below. Such contacting can be carried out by, for example, spraying the dehydrated cherries with an aqueous or other extract. After exposure to the extract, the enriched coffee cherries are subjected to a further dehydration step. For example, when the de-beaned coffee cherries that are dehydrating have reached a moisture content of 5-6%, the dehydrated coffee cherries can be sprayed using liquid coffee extract prepared as described herein or using methods known in the art, in a spray to enrich the powdered de-beaned coffee cherry product. For example, the spray amount can be about 0.1, 0.5, 0.75, 1, 1.25, 1.5, 2, 3, 4, 5, 10 or more ounces of extract per kilogram of dehydrated coffee cherry. For example, the spray amount can be approximately 1 (one) ounce of 50 BRIX extract for every kilogram of dried powder (based on 5-6% moisture). This enriched powder is dehydrated again until 5-6% moisture is reached (approximately 1-2 hour using methods disclosed herein).

Whether or not the coffee cherries are subjected to the optional enrichment step, the dehydrated cherries can then be ground into a powder. This grinding can be done using any method or machinery known in the art. For example, a Fitzpatrick Mill (Fitzmill) (Fitzpatrick Company. Elmhurst, Ind.) or HammerMill (Meadows Mills, Inc., North Wilkesboro, N.C.) can be used to grind the dehydrated coffee cherries into powder per customer specifications. The grinding step can be done using oxygen-free conditions.

Process for Preparing Liquid Extract

In another aspect, the invention provides a process for preparing an extract of coffee cherries, for example of de-beaned coffee cherries. For the extraction process, the de-beaning (if any), coating and storing (if any) steps are as described above for the preparation of a powder. In exemplary embodiments, the process uses coated de-beaned coffee cherries obtained without storage. In other exemplary embodiments, the process uses coated de-beaned coffee cherries that have been stored in oxygen-free and/or refrigerated conditions, either just in a refrigerated transport vehicle or also delivered to and stored in a refrigerated storage facility, as described previously. The extraction steps described herein can be performed once, or they can be performed multiple times, in order to achieve desired purity and yield.

In exemplary embodiments, the de-beaned coffee cherries are frozen before being subjected to the extraction process. Coated de-beaned coffee cherries to be extracted can be subjected to a maceration step. During the maceration step, the coffee cherries are chopped into fragments. The average size of the fragments can be, for example, less than about 5 cm, 4 cm, 3 cm, 2 cm, 1 cm, 9 mm, 8 mm, 7 mm, 6 mm, 5 mm, 4 mm, 3 mm, 2, mm, 1 mm, 0.5 mm, 0.1 mm or smaller, where the measurement reflects the largest dimension of length of the fragment. For example, the fragments can be about 0.5-2 mm or 1-2 mm. The maceration step can be performed using any means known in the art for such purpose. For example, a maceration tank. In some embodiments, the maceration tank contains one or more grinder/maceration pumps at the bottom, and can be airtight and oxygen-free using nitrogen to replace the oxygen. For example, the tank can hold the solvent, including an aqueous solvent such as purified water, at a ratio of approximately 1 gallon to 1 pound (liquid extract to de-beaned coffee cherry). In some embodiments, "grinder pumps" can be used to pump the liquefied material to a sealed extraction vessel for extraction. For example, the maceration step can be carried out in a maceration tank under oxygen-free conditions.

The macerated coffee cherry fragments can then be subjected to an extraction step. The extraction step can be carried out using any means known in the art that is suitable for extracting the antioxidants and/or other beneficial compounds in coffee cherries. For example, the coffee cherry fragments can be contacted with an aqueous solvent in an extraction tank. Other suitable solvents include methanol, ethanol, or a combination of either or both of methanol and ethanol with water. For example, the solvent can be about a 50/50 (measured by volume, by weight, or by w/v or v/w) mixture of water and ethanol, or water and methanol. The aqueous solvent can be, for example, water. The water can be purified water, and such purification can be carried out by any known method, including for example reverse osmosis, membrane filtering, charcoal bed filtering, deionization, distillation or a combination of these methods. For example, the aqueous solvent can be lab-quality water, prepared by subjecting it to reverse osmosis and then de-ionizing it. For example, the water can be prepared by subjecting it to reverse osmosis, membrane filtering and charcoal bed filtering to reach a high level of purity, e.g., <3 ppm, and then de-ionizing. The water or other extraction fluid can optionally contain additional preservatives such as ascorbic acid, citric acid or others known in the art. The extraction can also be done using ultra-high pressure extraction (known as UPE), which can be useful for extracting phenols or other antioxidants or beneficial compounds in coffee cherries. In UPE, high pressure can be used to "push" the solvent through the material without excessive heat that could cause degradation.

The temperature of the aqueous solvent can be an elevated temperature, for example above room temperature. The temperature of the aqueous solvent can be, for example, at least about 70° F., 80° F., 90° F., 100° F., 110° F., 120° F., 130° F., 140° F., 145° F., 150° F., 155° F., 160° F., 170° F., 180° F., 190° F., 200° F., 210° F. or higher. The amount of water used in the extraction can be expressed as a ratio versus the coffee cherry fragments. For example, the aqueous solvent:fragment ratio (in units of gallons solvent: pounds fragment) can be at least about 0.01:1, 0.1:1, 0.2:1, 0.3:1, 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1 or higher. The extraction can be carried out under oxygen-free conditions.

During extraction, the solvent/fragment mixture can optionally be agitated. Agitation can be carried out by any method known in the art, for example by mechanical agitation (e.g., motor and blades), ultrasonic agitation (using, e.g., an ultrasonic transducer), and/or enzymatic agitation (by using introduced enzymes in accordance with methods known in the art). For example, the mixture can be agitated using mechanical agitation. Such mechanical agitation can be accomplished using a Lightnin agitator (Lightnin, Rochester, N.Y.). The mixture can be agitated for a period of time, so as to facilitate the extraction process. For example, the mixture can be agitated for at least about 1 minute, 5 minutes, 10 minutes, 15 minutes, 20 minutes, 25 minutes, 30 minutes, 35 minutes, 40 minutes, 45 minutes, 50 minutes, 55 minutes, 1 hour, 1 hour 30 minutes, 2 hours, 3 hours or longer. The mixture can, for example, be agitated for about 40 minutes.

The solvent/fragment mixture can be filtered to remove particulate matter, including coffee cherry pulp sediment. Filtration methods are known in the art, and a person of ordinary skill can choose the appropriate filtration method from among those known. Non-limiting examples of such filtration methods include: 1) membrane filtration, such as microfiltration, ultrafiltration, nanofiltration, and reverse osmosis with either spiral-wound, stainless steel, ceramic, tubular, or plate-and-frame configurations; 2) sediment clarifying, whereby a food-grade tank can be employed to hold the extract under oxygen-free conditions to allow sediment to collect at the bottom of the tank due to gravity, for example for a period of approximately 24 hours, and removing the bottom sediment via a separator valve; 3) press and filter methods, whereby a mechanical, pneumatic or hydraulic press can be employed to squeeze the clear juice through a sieve or a series of sieves, or screen with less than 5 microns in size to eliminate sediment; 4) centrifugation, whereby a centrifuge can be used to separate the solids by centrifugal force; and 5) vacuum filtration, which can provide another oxygen free filtration method. For example, the solvent/fragment mixture can be filtered using a press and filter method. The filtrate can then be collected in a container such as a food-grade holding tank, in which it can be stored under oxygen-free conditions. The holding tank can also be used for clarifying/filtering by gravity separation (described below), or for overflow management, e.g. if too much liquid is being processed for the evaporators to keep up, or if the evaporators are operating at full capacity. Particulate matter can also or additionally be removed by sedimentation, i.e. by allowing the mixture to stand and the particulate matter to settle to the bottom of the storage vessel, using methods such as those described above. After sedimentation, the supernatant liquid is removed for further processing. The supernatant liquid can optionally be filtered. Sedimentation, if used, can also be conducted under oxygen-free conditions, for example under a blanket of inert gas. The fluids and filtrate at this point can be referred to as a dilute extract.

The particulate matter collected during filtration can optionally be processed further in a fruit/herb press, for example a pneumatic press of 10 tons capacity (Eden Labs, Tacoma, Wash.), a hydraulic press, or similar device to generate additional fluid. The fluid generated by pressing the particular matter can then be added to the filtrate generated during the filtration step and added to the dilute extract.

The dilute extract can be subjected to an evaporation step. The evaporation step results in a more concentrated extract. Extract concentration is monitored using BRIX measurements. BRIX values are generally used to measure sugar concentration in a liquid, but they can also be used as a proxy for extract concentration: the higher the BRIX value, the more concentrated the extract. The dilute extract can have a low BRIX value, for example less than about 10 BRIX, 8 BRIX, 6 BRIX, or 4 BRIX or lower, or between about 0.1 and 10 BRIX, 1 and 5 BRIX, and 1 and 3 BRIX, or about 1.5 to about 2.5 BRIX. The BRIX value of the concentrated extract can be up to or at least about 1.5 BRIX, 2.5 BRIX, 5 BRIX, 10 BRIX, 15 BRIX, 20 BRIX, 25 BRIX, 30 BRIX, 35 BRIX, 40 BRIX, 45 BRIX, 50 BRIX, 55 BRIX, 60 BRIX, 65 BRIX, 70 BRIX, 75 BRIX, 80 BRIX, 85 BRIX, 90 BRIX, 95 BRIX, 100 BRIX or higher, or between about 30 and 70 BRIX, or 30 and 60 BRIX, or 40 and 60 BRIX, or about 50 BRIX. The extract can be reduced by a ratio of up to about 5:1, about 10:1, about 15:1, about 20:1, about 25:1, about 35:1, about 40:1, about 45:1, about 50:1, about 60:1 or higher (where the ratio indicates initial versus final volume). BRIX measurements can be conducted using a "Brix Meter" or "Refractometer." The liquid extract can be concentrated to any desired level, from a relatively dilute extract to a very concentrated and viscous extract and even subjected to complete evaporation (for example less than about 10% moisture content, or about 5-6% moisture content or below) to provide a dry extract concentrate.

The evaporation step can be conducted using any means and methods known in the art, for example using a tube falling film evaporator, plate evaporator, a spinning band column evaporator or a spinning cone evaporator. In a tube falling film evaporator, the juice to be evaporated is distributed onto an upper tube sheet and onto heating tubes by an especially developed distribution system. From this system, the product flows downwards in the heating tubes to a lower tube sheet as a thin film. The evaporated vapor (steam) flows downwards in the same direction and consequently accelerates the flowing of the film. This limits the period of residence, during which the juice to be evaporated is retained in the heating tube, to a few seconds. In a plate evaporator, the main feature is the compact design. The constructional height ranges from 3 to 5 meters depending on the design. Plate evaporators normally are designed for rising flow in single-pass operation. This keeps the thermal strain on the product as low as possible. Concentration of clear juice, or juice containing little pulp, are examples of application in the fruit juice industry. The spinning cone evaporator is a compact unit well-suited for the concentration of heat-sensitive, valuable and viscous products. It offers a short residence time, less thermal impact and greater processing flexibility than traditional rising or falling film evaporators. For example, the evaporation can be done using a spinning cone evaporator, such as Centritherm® evaporator (FT Technologies, Griffith, Australia). In exemplary embodiments, the evaporation step is conducted under low temperature conditions and/or at reduced pressure. As used here, low temperature means a temperature less than or about 100° C., 90° C., 80° C., 70° C., 69° C., 68° C., 67° C., 66° C., 65° C., 64° C., 63° C., 62° C., 61° C., 60° C., 59° C., 58° C., 57° C., 56° C., 55° C., 50° C. or lower, or about 50-100° C., 50-80° C., or 60-70° C. For example, the evaporation can be done at about 62° C. For example, the evaporation can be done under low-temperature and oxygen-free conditions. Evaporation can be carried out using vacuum-based techniques. The resulting concentrated extract can be stored under oxygen-free and/or refrigerated conditions, and can also be pasteurized if desired.

The following examples are provided in order to better enable one of ordinary skill in the art to make and use the disclosed compositions and methods, and are not intended to limit the scope of the invention in any way.

EXAMPLES

Example 1

Preparation of Powder

Collection of De-Beaned Coffee Cherries:

Coffee cherries were de-beaned cherry using a method called "pulping" where the machine called a coffee pulper gently "pinches out" the bean from the fruit. The de-beaned coffee cherries were sprayed within seconds of being pulped, as they travel through a skin disposal auger (about a 10 second ride through the auger). Coated de-beaned coffee cherries from the ejection end of the auger were placed into food-grade poly bags, and the bags were then vacuumed and sealed. The bags were then immediately loaded into a refrigerated vehicle until the collection is finished. The temperature inside the refrigerated vehicle storage is approximately 32 degrees F. The bags are transported in the refrigerated vehicle to a storage facility, where the bags were stored under refrigerated conditions. The bags were kept from direct sunlight from the time of collection on.

Processing De-Beaned Coffee Cherries Prior to Powder Formation:

De-beaned coffee cherries were placed on an inspection conveyor inside a refrigeration room where they were inspected for quality, debris, twigs, and seeds. De-beaned coffee cherries were then conveyed to a blanching tank containing hot water at about 190 degrees F., in which they were dipped for approximately 45 seconds in order to neutralize enzymes. The blanched coffee cherries were then dipped in a cool solution of ascorbic acid/citric acid so as to not "cook" the phenols.

Dehydrating Processed Coffee Cherries:

The blanched coffee cherries were then placed on a shaker/vibrator conveyor (under oxygen-free conditions) to remove excess fluid and then loaded into dehydrators. The dehydrators were low temperature, stainless steel, commercial dehydrators made by Commercial Dehydrator Systems, Inc. (Eugene, Oreg.), similar to the EXCALIBER™ dehydrator or the Klamath, that has been modified to eliminate oxygen. The air intake is hooked up to a nitrogen generator to eliminate oxygen in the dehydrator. The dehydrators were sealed and operated using low heat, and nitrogen was circulated in the dehydrators oxygen to inhibit enzyme activity during the dehydration step. The blanched coffee beans were dried for approximately 10-12 hours at about 140 degrees F. to a water content of less than 6% (w/w).

Powder Formation:

Dehydrated coffee cherries were ground using a Fitzpatrick Mill (Fitzmill) Powder Grinding Machine into powder. The FitzMill was enclosed in an oxygen free environment while operating to eliminate product degradation.

Example 2

Preparation of Powder Using Citric Acid/Ascorbic Acid Dip

The de-beaned coffee cherries were processed according to Example 1, except that instead of blanching the de-beaned coffee cherries, the de-beaned coffee cherries were dipped for 45 seconds in a submersion tank containing a solution of ascorbic acid and citric acid (about 7 grams citric acid and about 15 grams ascorbic acid per gallon of water), which was heated to about 185° F.

Example 3

Preparation of Fortified Powder

Prior to grinding the de-beaned coffee cherries, they were enriched by spraying them with 50 BRIX extract prepared in accordance with Example 4, below. The enriched composition was then returned to the dehydrators to re-dry.

Example 4

Powder Preparation without Freezing

The de-beaned coffee cherries were processed according to the "Collection of De-Beaned Coffee Cherries" step of Example 1, except that the de-beaned cherries were never delivered to a storage facility for freezing. Instead, they were loaded into the refrigerated vehicle and delivered to a production plant.

At the production plant, the de-beaned coffee cherries are removed from the scaled bags, then spread onto dehydration trays for inspection. They are then blanched, then cold dipped to arrest cooking, then the excess water is shaken off before loading the tray into the dehydrator for further processing as set forth in Example 1.

Example 5

Preparation of Liquid Extract

Collection of De-Beaned Coffee Cherries:

The coffee cherries were de-beaned, coated and stored as set forth in Example 1.

Processing of De-Beaned Coffee Cherries Prior to Extraction:

De-beaned coffee cherries were placed on an inspection conveyor inside a refrigeration room where they were inspected for quality, debris, twigs, and seeds. De-beaned coffee cherries for use in liquid extraction were conveyed to a maceration tank under oxygen-free conditions, where they are chopped to a size of 0.5-2 mm.

Extraction:

An extraction tank was filled with lab-quality water, prepared by subjecting it to reverse osmosis and then de-ionization. Water was then heated to 145° F. (63° C.). Macerated coffee cherry fragments were added to the water-filled extraction tank in a ratio of 1:1 (gallons water/pounds fragments). The extraction tank was vacuumed to remove all oxygen, and then agitated with a Lightnin Mixer agitator (Lightnin, Rochester, N.Y.) for about 40 minutes. The water/fragment mixture was then filtered by use of a 25 micron stainless steel screen filter and the filtrate was conveyed to a receiving tank. The extracted skins removed via filtration were conveyed to a fruit press, which squeezed out any remaining fluid. Pressed fluid was then filtered as above, and piped to the receiving tank. The receiving tank, which is food-grade, was sealed and vacuumed. All steps were carried out under oxygen-free conditions.

Evaporation:

The extract produced thus far had a BRIX measurement of approximately 1.5 to 2.5. Evaporation was conducted at approximately 145 degrees F. using oxygen-free conditions (achieved using a vacuum). The extract was evaporated with a material residence time of 1 second. The extract's BRIX value was measured as evaporation is taking place. Once a BRIX level of 50 was achieved, the concentrated extract was sealed in tanks under oxygen-free conditions, with nitrogen used to replace oxygen. The 50 BRIX extract was then transported to refrigeration rooms.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A process for preparing an antioxidant-rich powder, comprising the steps of:
   providing ripe de-beaned coffee cherries;
   contacting the de-beaned coffee cherries with a coating solution comprising citric acid and ascorbic acid within about one hour after the coffee cherries are de-beaned to produce a coated de-beaned coffee cherry;
   dehydrating the coated de-beaned coffee cherries; and
   grinding the dehydrated de-beaned coffee cherries to form an antioxidant-rich powder.

2. The process of claim 1, wherein the de-beaned coffee cherries are contacted with the coating solution within one minute after the coffee cherries are de-beaned.

3. The process of claim 1, further comprising a step of storing the coated de-beaned coffee cherries under refrigerated conditions and conditions in which the de-beaned coffee cherries are protected against exposure to oxygen prior to dehydrating the coated de-beaned coffee cherries.

4. The process of claim 3, wherein storing the coated de-beaned coffee cherries under conditions in which the de-beaned coffee cherries are protected against exposure to oxygen comprises:
   placing the coated de-beaned coffee cherries in a container to produce a filled container within about 15 minutes after the coffee cherries are coated;
   removing oxygen from the filled container; and
   sealing the filled container.

5. The process of claim 3, wherein the container is sealed within five minutes after the coffee cherries are coated.

6. The process of claim 3, wherein refrigerated conditions comprise temperatures below about 32° F.

7. The process of claim 1, further comprising the step of blanching the coated de-beaned coffee cherries.

8. The process of claim 7, wherein blanching comprises exposing the coated de-beaned coffee cherries to water at a temperature of about 190° F. for about 45 seconds.

9. The process of claim 1, further comprising the step of contacting the coated de-beaned coffee cherries with a solution comprising citric acid and ascorbic acid.

10. The process of claim 9, wherein the coated de-beaned coffee cherries are contacted with the solution comprising citric acid and ascorbic acid for about 1-2 minutes.

11. The process of claim 1, wherein the step of dehydrating the coated de-beaned coffee cherries comprises subjecting the coated de-beaned coffee cherries to a temperature of about 135° F. for about 10-12 hours.

12. The process of claim 1, further comprising the step of contacting the dehydrated de-beaned coffee cherries with an antioxidant-rich coffee extract.

13. The process of claim 1, wherein the coating solution comprising ascorbic acid and citric acid comprises about 15 grams ascorbic acid and about 7 grams citric acid per gallon of water.

14. The process of claim 1, wherein the coated de-beaned coffee cherries are dehydrated under conditions in which the de-beaned coffee cherries are protected against exposure to oxygen.

15. A process for preparing an antioxidant-rich powder, comprising the steps of:
   providing ripe de-beaned coffee cherries;
   applying a coating solution comprising citric acid and ascorbic acid to the de-beaned coffee cherries within about one hour after the coffee cherries are de-beaned to produce a coated de-beaned coffee cherry;
   thereafter placing the coated de-beaned coffee cherries in a container to produce a filled container;
   removing oxygen from the filled container;
   sealing the filled container;
   storing the filled container under refrigerated conditions;
   removing the coated de-beaned coffee cherries from storage;
   blanching the coated de-beaned coffee cherries;
   dehydrating the coated de-beaned coffee cherries to provide dehydrated coffee cherries;
   enriching the dehydrated coffee cherries by contacting the dehydrated coffee cherries with an antioxidant-rich coffee extract; and grinding the dehydrated de-beaned coffee cherries to form an antioxidant-rich powder;

wherein the coated de-beaned coffee cherries are blanched and dehydrated under conditions in which the de-beaned coffee cherries are protected against exposure to oxygen.

16. A process for preparing an antioxidant-rich coffee extract, comprising the steps of:

providing ripe de-beaned coffee cherries;

contacting the de-beaned coffee cherries with a coating solution comprising citric acid and ascorbic acid within about one hour after the coffee cherries are de-beaned to produce a coated de-beaned coffee cherry; and extracting the antioxidants from the coated de-beaned coffee cherries to produce an antioxidant-rich coffee extract and extracted coffee cherries.

17. The process of claim 16, further comprising a step of storing the cherries under refrigerated conditions and conditions in which the de-beaned coffee cherries are protected against exposure to oxygen prior to extracting antioxidants from the coated de-beaned coffee cherries.

18. The process of claim 17, wherein storing the coated de-beaned coffee cherries under conditions in which the de-beaned coffee cherries are protected against exposure to oxygen comprises:

placing the coated de-beaned coffee cherries in a container to produce a filled container within about 15 minutes after the coffee cherries are coated;

removing oxygen from the filled container; and sealing the filled container.

19. The process of claim 17, wherein refrigerated conditions comprise temperatures below about 25° F.

20. The process of claim 16, wherein extracting the antioxidants comprises:

macerating the coated de-beaned coffee cherries to produce coffee cherry fragments; and contacting the coffee cherry fragments with an aqueous solvent.

21. The process of claim 20, wherein the average size of the coffee cherry fragments is about 1-2 $mm^2$ in size.

22. The process of claim 20, wherein the macerating step is conducted under conditions in which the de-beaned coffee cherries are protected against exposure to oxygen.

23. The process of claim 20, wherein the contacting step is conducted under conditions in which the de-beaned coffee cherries are protected against exposure to oxygen.

24. The process of claim 20, wherein the aqueous solvent comprises purified water.

25. The process of claim 24, wherein the purified water has been subjected to reverse osmosis and deionized.

26. The process of claim 20, aqueous solvent is heated to a temperature of at least about 140° F.

27. The process of claim 20, wherein the coffee cherry fragments and the aqueous solvent are in a weight:gallon ratio of about 1:1.

28. The process of claim 20, further comprising the step of agitating the macerated coffee cherry fragments and aqueous solvent.

29. The process of claim 20, further comprising filtering the macerated coffee cherry fragments and aqueous solvent.

30. The process of claim 16, comprising the step of pressing the extracted coffee cherries to remove fluid.

31. The process of claim 16, comprising the step of pressing the extracted coffee cherries to remove fluid, wherein the fluid removed during the pressing step is filtered and combined with the extract.

32. The process of claim 16, further comprising the step of evaporating the extract to produce a concentrated extract.

33. The process of claim 32, wherein the concentrated extract has a BRIX value of at least about 30.

\* \* \* \* \*